United States Patent
Moi

[19]

[11] Patent Number: 6,036,021
[45] Date of Patent: Mar. 14, 2000

[54] PACKAGE FOR ELECTROPHORESIS GEL

[75] Inventor: Min Kar Moi, San Diego, Calif.

[73] Assignee: C.C. Imex, San Diego, Calif.

[21] Appl. No.: 09/251,510

[22] Filed: Feb. 17, 1999

[51] Int. Cl.[7] .................................................. B65D 69/00
[52] U.S. Cl. .......................... 206/570; 206/363; 53/468; 204/456; 204/616
[58] Field of Search .................... 206/461, 462, 206/467, 470, 471, 570, 232, 525, 438, 363; 53/467, 468; 204/456, 466, 606, 616, 618

[56] References Cited

U.S. PATENT DOCUMENTS

| | | |
|---|---|---|
| 3,129,158 | 4/1964 | Raymond et al. . |
| 3,442,686 | 5/1969 | Jones . |
| 3,932,263 | 1/1976 | Brefka . |
| 4,437,568 | 3/1984 | Hamblin ................................. 206/570 |
| 4,501,363 | 2/1985 | Isbey, Jr. ................................ 206/570 |
| 4,548,869 | 10/1985 | Ogawa et al. . |
| 4,548,870 | 10/1985 | Ogawa et al. . |
| 4,576,693 | 3/1986 | Kreisher et al. . |
| 4,579,783 | 4/1986 | Ogawa et al. . |
| 4,600,641 | 7/1986 | Ogawa et al. . |
| 4,681,223 | 7/1987 | Roberts .................................. 206/470 |
| 4,718,998 | 1/1988 | Ogawa et al. . |
| 4,722,777 | 2/1988 | Ogawa et al. . |
| 4,729,823 | 3/1988 | Guevara, Jr. . |
| 4,737,258 | 4/1988 | Ogawa et al. . |
| 4,737,259 | 4/1988 | Ogawa et al. . |
| 4,762,743 | 8/1988 | von Alven et al. . |
| 4,833,332 | 5/1989 | Robertson, Jr. et al. . |
| 4,834,854 | 5/1989 | Sugihara et al. . |
| 4,844,786 | 7/1989 | Sugihara et al. . |
| 4,897,306 | 1/1990 | Sugimoto et al. . |
| 4,904,366 | 2/1990 | Tokita et al. . |
| 4,954,236 | 9/1990 | Kushner et al. . |
| 5,084,356 | 1/1992 | Deak et al. . |
| 5,085,904 | 2/1992 | Deak et al. . |
| 5,090,568 | 2/1992 | Tse ......................................... 206/470 |
| 5,190,629 | 3/1993 | Sugihara et al. . |
| 5,190,632 | 3/1993 | Fujimiya et al. . |
| 5,230,781 | 7/1993 | Middendorf et al. . |
| 5,293,993 | 3/1994 | Yates, Jr. et al. ....................... 206/470 |
| 5,311,990 | 5/1994 | Kalinski ................................. 206/570 |
| 5,372,269 | 12/1994 | Sutton et al. . |
| 5,498,475 | 3/1996 | Takigawa et al. . |
| 5,685,967 | 11/1997 | Manis et al. . |
| 5,785,835 | 7/1998 | Saito et al. . |

OTHER PUBLICATIONS

Vitor M.C. Madeira et al. "Bargain Electrophoresis". Journal of Chemical Education, vol. 63, No. 12, pp. 1109–1111. Dec. 1986.

*Primary Examiner*—Paul T. Sewell
*Assistant Examiner*—Luan K. Bui
*Attorney, Agent, or Firm*—John L. Rogitz

[57] ABSTRACT

An electrophoresis gel package includes a unitary PVC housing including a cover joined to a holder by a living hinge. A tray that has gel disposed thereon is received into the holder, and the cover then moved to engage the holder and protectively enclose the gel. The housing includes structure which cooperates to limit unintended motion of the gel relative to the tray and to the housing.

18 Claims, 2 Drawing Sheets

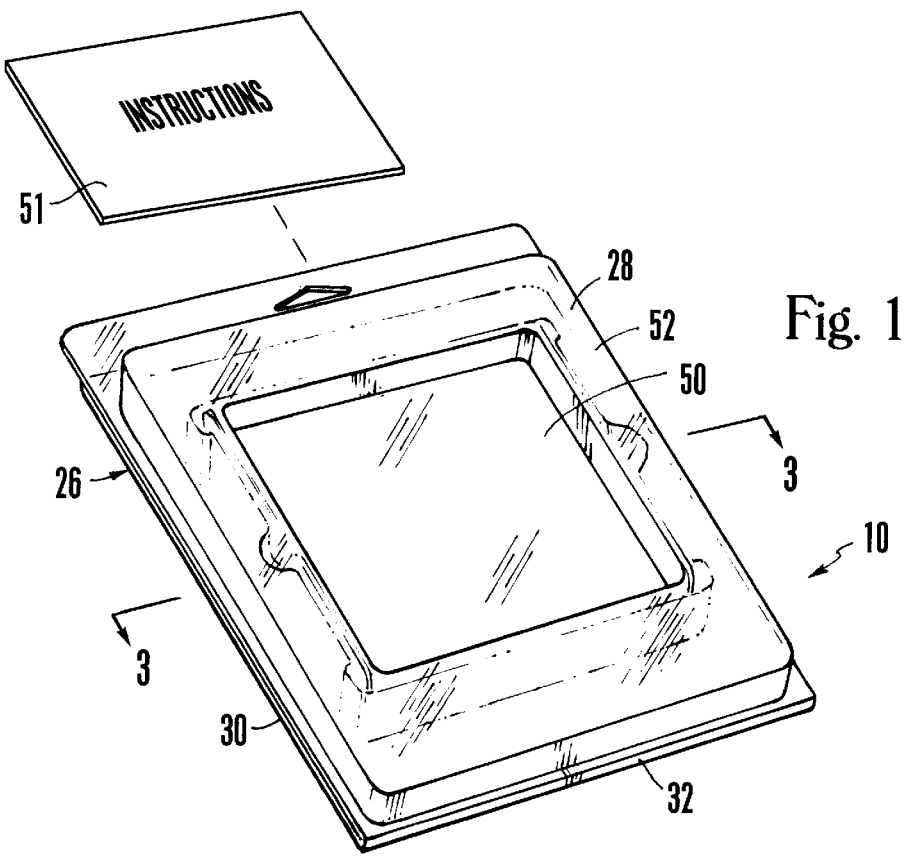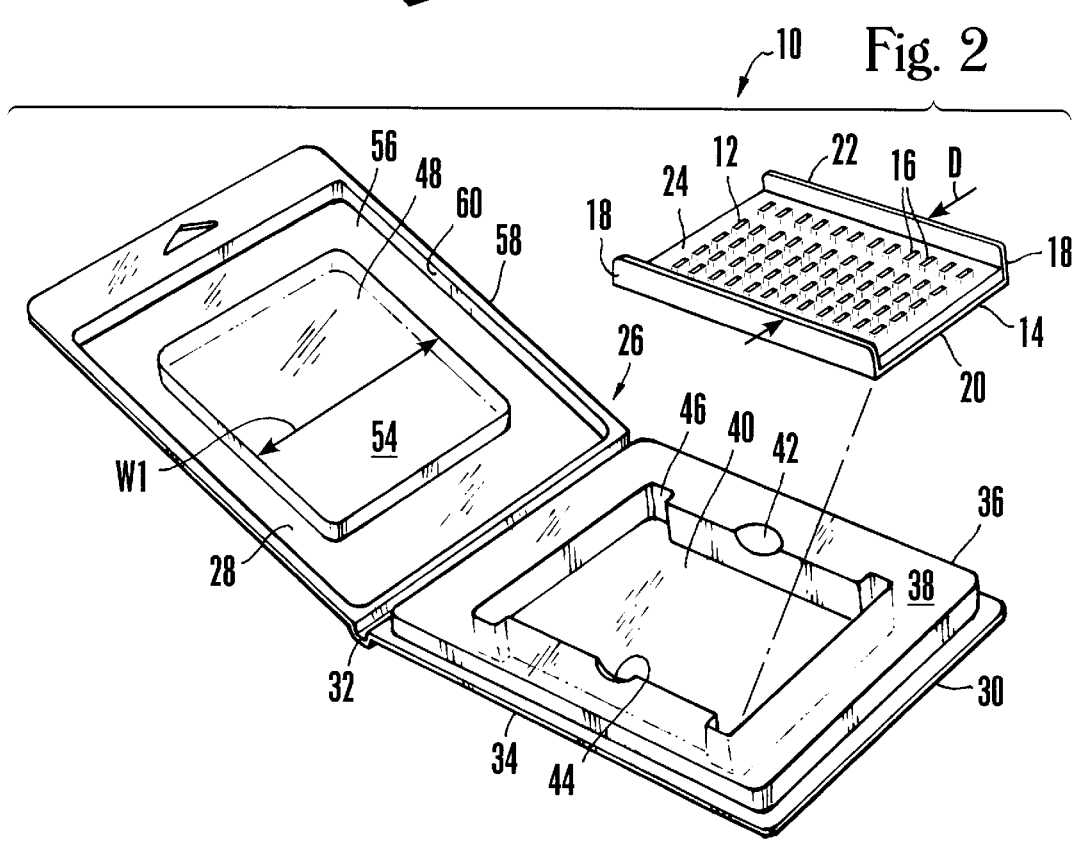

PACKAGE FOR ELECTROPHORESIS GEL

FIELD OF THE INVENTION

The present invention relates generally to methods and apparatus for analyzing substances such as DNA, and more particularly to methods and apparatus for holding electrophoresis gels to protect the gels for use.

BACKGROUND

Electrophoresis is used for many purposes, including for analysis of substances such as deoxyribonucleic acid (DNA) to gain a clearer understanding of the nature and role of genes that are carried by DNA. Indeed, electrophoresis is among the most widespread of DNA analyzing methods.

In gel electrophoresis, a gel is provided, and a sample to be analyzed is deposited on the gel, typically in a rectangular-shaped cavity in the gel referred to as a sample well. Usually the gel is held by a tray, and the tray is placed in a buffer chamber consisting of an anode and a cathode. A liquid buffer solution is added to establish electrical contact between the electrodes and the gel. Then, an electric field is applied to the gel. The various genetic constituents of the sample migrate through the gel under the influence of the electric field at varying rates, depending on their sizes, essentially establishing a genetic spectrum in the gel. This spectrum can be observed and the genetic constituents of the sample determined.

Agarose gel is widely used in the field of molecular biology. To make an agarose gel, the gel can be formed in the tray, and then packaged for shipment to a laboratory or other user. The package typically includes a four-sided semi-rigid plastic bottom into which the gel is laid, and a flaccid paper or foil cover to cover the gel to establish a blister pack type of package. When received, the cover is peeled away from the bottom and the gel can then be used. Representative of such a package is that marketed by FMC Bioproducts of Rockland, ME under the trade name "Reliant Gel System".

As recognized herein, the above-described blister pack requires the bottom to have four sides, to support the gel and flaccid cover. As also understood herein, two of the sides, which can be thought of as the front and rear sides, interfere with subsequent electrophoresis of the gel. Thus, using the above-described structure, either electrophoresis is interfered with, or the gel must be removed from the bottom prior to electrophoresis and placed in another support structure, thereby requiring additional steps on the part of the user.

Moreover, the present invention understands that the use of a flaccid cover that can be easily depressed or otherwise deformed into the gel even when the cover is held in a somewhat taut configuration on the semi-rigid plastic bottom can result in damaging the gel. The present invention, having understood the desirability of securely shipping gels while minimizing handling of the gels, addresses one or more of the above-noted considerations.

SUMMARY OF THE INVENTION

A shipping package for an electrophoresis gel includes the gel, and a housing defining a cover and a holder. The holder in turn defines an interior that surrounds the gel, and a hinge joins the cover to the holder to permit moving the cover relative to the holder between a closed configuration of the housing, wherein the gel is not exposed and wherein the gel is closely held in the housing, and an open configuration of the housing, wherein the gel is exposed for removal of the gel from the holder.

In the preferred embodiment, a tray holds the gel. In accordance with the preferred embodiment, the tray is received in the interior of the holder. Preferably, the tray is made of a rigid UV transparent material and the housing is made of a single unitary piece of semi-rigid plastic such as polyvinylchloride.

As disclosed in detail below, the tray defines a contour, and the interior of the holder includes a cavity having a contour configured like the contour of the tray. As intended herein, the cavity is marginally larger than the tray to limit motion of the tray relative to the housing. If desired, the contour of the cavity can include opposed finger depressions for receiving a person's fingers therein to permit the person to grip the tray to remove the tray from the holder.

In accordance with the present invention, the tray includes one or more side walls, with each side wall defining a respective top edge. The gel is disposed in the tray below the top edges of the side walls, and the cover is formed with a land that is closely receivable between the side walls when the housing is in the closed configuration. The land defines a bottom surface, and the bottom surface is closely spaced from the gel when the housing is in the closed configuration to thereby limit motion of the gel within the package. To limit motion of the tray within the housing, the cover defines a surface bounding the land, and at least a portion of the surface contacts the top edges of the side walls of the tray when the housing is in the closed configuration.

The cavity of the holder is bounded by a surface defining an outer periphery. As provided herein, the surface of the cover is bounded by one or more raised outer edges, and the periphery of the surface of the holder engages the raised edges of the cover in an interference fit to hold the housing in the closed configuration.

In another aspect, a gel kit for protectively shipping electrophoresis gel includes a tray, an electrophoresis gel disposed in the tray, and a non-flaccid clamshell selectively holding the tray with gel.

In still another aspect, a method for transporting electrophoresis gel includes providing a plastic housing having an open configuration and a closed configuration. The method further contemplates moving the housing to the open configuration, disposing the gel in the housing, and then moving the housing to the closed configuration to completely enclose the gel.

The details of the present invention, both as to its structure and operation, can best be understood in reference to the accompanying drawings, in which like reference numerals refer to like parts, and in which:

BRIEF DESCRIPTION OF THE DRAWINGS

FIG. 1 is a perspective view of the present container in the closed configuration, with a booklet of operating instructions shown in an exploded relationship with the depression of the cover;

FIG. 2 is a perspective view of the container in the open configuration, in an exploded relationship with gel and tray;

DETAILED DESCRIPTION OF THE PREFERRED EMBODIMENT

Figure 3:
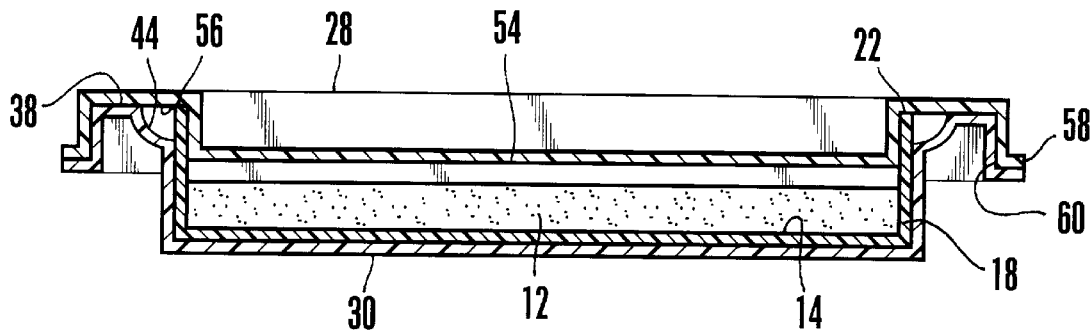
FIG. 3 is a cross-sectional view as seen along the line 3—3 in FIG. 1.

Referring now to FIGS. 1–3, a package is shown, generally designated 10, for holding an electrophoresis gel 12.

The gel 12 can be an agarose gel, or it can be another type of gel, such as a polyacrylamide gel, that is made in accordance with means known in the art. If desired, the gel 12 can be formed on or later placed on a tray 14, with the gel 12 being formed with sample wells 16 if desired.

In the preferred embodiment, the tray 14 is made of a UV-transparent material, to promote subsequent electrophoresis analysis. In a particularly preferred embodiment, the tray 14 is made of transparent hard rigid plastic, such as acrylic. If desired, other suitable materials can be used, such as glass.

In any case, the tray 14 preferably is generally rectangular as shown, although it can assume other shapes as may be desirable for engagement with an electrophoresis apparatus. As shown in FIG. 2, the tray 14 is formed with at least one, and more preferably two opposed co-parallel elongated side walls 18 that rise perpendicularly upwardly from a bottom 20 of the tray 14. Each wall 18 defines a respective top edge 22, with the top edge 22 of each wall 18 being positioned above a top surface 24 of the gel 12 as shown. No front or read walls need be provided on the tray 14 as shown, however, rendering the tray 14 more suitable for supporting the gel 12 during electrophoresis than trays that must have four walls to support blister packaging.

As can be appreciated in reference to FIGS. 1 and 2, the tray 14 with gel 12 is closely held within a package housing, generally designated 26. The package housing 26 is preferably a hollow, generally parallelepiped-shaped structure, although it can assume other shapes. In one preferred embodiment, the package housing 26 is made of a transparent semi-rigid material such as polyvinylchloride. If desired, the housing 26 can be made of semi-rigid materials other than PVC. Indeed, the housing 26 can be made of rigid material such as acrylic, plexiglass, or even glass. From another standpoint, the entire housing 26 is non-flaccid, in contrast to, e.g., paper or foil.

As shown in the preferred embodiment depicted in the Figures, the housing 26 is made of a unitary piece of material, and it includes a cover 28 that is joined to a holder 30 along a living hinge 32. With this structure, the housing 26 can be moved between the closed configuration shown in FIG. 1 and the open configuration shown in FIG. 2. In the closed configuration shown in FIG. 1, it will readily be appreciated that the gel is closely held in the housing and is not exposed, although it may be visible through the transparent housing 26. On the other hand, in the open configuration the gel is exposed for removal thereof from the holder. In less preferred embodiments, the cover 28 can be made separately from the holder 30 and then snappingly or otherwise engaged with the holder 30 (e.g., in an interference fit, or by means of a detent-cavity structure or clip structure) to hold the two parts together.

Returning to the preferred embodiment shown in the Figures, the holder 30 includes a bottom surface 34 and a parallelepiped-shaped cavity structure 36 rising upwardly from the bottom surface 34. The cavity structure 36 defines a cavity structure surface 38 that is parallel to the bottom surface 34. At least one cavity 40 is centrally located in the cavity structure surface 38, although it is to be understood that additional cavities can be formed side by side in a single housing for holding additional trays in accordance with present principles. With the exceptions noted below, the cavity 40 is parallelepiped-shaped, although it can assume other shapes. In any case, the cavity 40 is formed for closely receiving the tray 14. Thus, the cavity 40 has a contour that is configured like the contour of the tray 14, with the size of the cavity 40 being marginally larger than the size of the tray 14. With this structure, the tray 14 cannot move side to side in the cavity 40, although the interference between the tray 14 and cavity 40 walls does not impede a person's ability to extract the tray 14 from the cavity 40.

Further to this end, in a particularly preferred embodiment the contour of the cavity 40 includes opposed finger depressions 42, 44 that are formed partially in the cavity structure surface 38 for receiving a person's fingers therein. This facilitates person gripping the tray 14 to remove the tray 14 from the holder 30. Also, corner extensions 46 can be formed in the four corners of the otherwise rectangular (in cross-section) cavity 40 as shown.

Turning now to the cover 28, as shown best in FIGS. 2 and 3, the cover 28 is formed with a paralellepiped-shaped land 48 which is closely receivable between the side walls 18 of the tray 14 when the housing 26 is in the closed configuration. In cross-reference to FIGS. 1 and 2, the land 48 is established by forming an inwardly-depending parallelepiped-shaped depression 50 in a top surface 52 of the cover 28, it being understood that the land 48 is the opposite (inner) side of the depression 50. In any case, the width "W" of the land 48 is marginally less than the distance "D" between the side walls 18 of the tray 14. In addition to the advantages noted below, the depression 50 establishes a resting place for gel/tray/package operating instructions 51 in booklet or pamphlet form, as can be appreciated in reference to FIG. 1.

FIG. 2 shows that the land 48 defines a bottom surface 54. As can be appreciated best in reference to FIG. 3, the land 48 is configured such that when the housing 26 is in the closed configuration, the bottom surface 54 is closely spaced from the gel 12 (e.g., by about two millimeters) to thereby limit motion of the gel 12 within the package. Specifically, it is possible that the gel 12 can fall out of the tray 14 when the package 10 is inverted, thereby becoming damaged. The close spacing of the bottom 54 from the gel 12 impedes motion of the gel 12 relative to the tray 14 (and housing 26) under such circumstances.

Additionally, in the preferred embodiment the underside of top surface 52 of the cover 28 establishes an inner surface 56 that bounds the land 48. FIG. 3 shows that a portion of the inner surface 56 contacts the top edges 22 of the side walls 18 of the tray 14 when the housing 26 is in the closed configuration. This impedes if not prevents relative motion of the tray 14 vis-a-vis the housing 26. Moreover, the inner surface 56 of the cover 28 is bounded by one and preferably by four raised edges 58 as shown. The inner walls 60 of the raised edges 58 can engage the periphery of the cavity structure surface 38 of the holder 30 in an interference fit to hold the housing 26 in the closed configuration.

With the above-described cooperation of structure, the cover 28 can be moved away from the holder 30 about the hinge 32 to open the package 10. Then, the tray 14 with gel 12 is placed in the cavity 40, and the cover 28 engaged with the holder 30 as described above to completely enclose the tray 14, as shown in FIG. 1. In the closed configuration, with the land 48 within the cavity 40 and closely spaced from the gel 12, and with the inner surface 56 of the cover 28 contacting the top edges 22 of the side walls 18 of the tray 14, neither the tray 14 nor the gel 12 can move relative to the housing 26 any appreciable distance, if at all. Moreover, because it is at least semi-rigid the housing 26 protects the gel 12, since the housing 26 cannot be easily deformed to the point where it is compressed into the gel 12. Consequently, the gel 12 with tray 14 are held securely within the housing 26.

Figure 4:
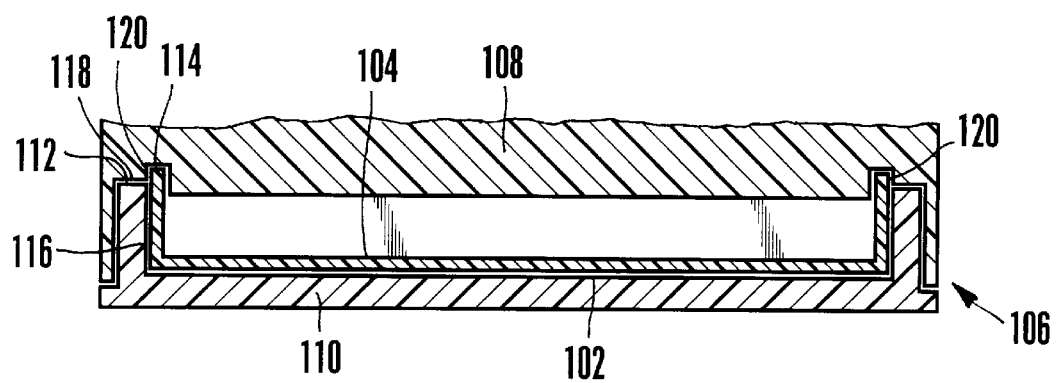
FIG. 4 is a cross-sectional view of an alternate embodiment as would be seen along the line 3—3 in FIG. 1, with portions broken away.

FIG. 4 shows a package 100 that includes a tray 102 holding a gel 104 in a housing 106 that includes a cover 108 and a holder 110 which is in all essential respects identical to the package 10 shown in FIGS. 1–3, with the following exceptions. The top surface 112 of the holder 110 does not extend to the top edges 114 of the side walls 116 of the tray 102. A cover surface 118, however, is closely juxtaposed with the top surface 112 when the housing 106 is in the closed configuration, with opposed elongated grooves 120 being formed in the cover 108 as shown for receiving the top portions of the side walls 116, including the top edges 114. With this structure, the tray 102 is securely held when the housing 106 is in the closed configuration, and no finger depressions are required in the holder 110. Instead, when the housing 106 is opened, the top edges of the side walls 116 can be easily grasped by a person for removing the tray 102.

While the particular PACKAGE FOR ELECTROPHORESIS GEL as herein shown and described in detail is fully capable of attaining the above-described objects of the invention, it is to be understood that it is the presently preferred embodiment of the present invention and is thus representative of the subject matter which is broadly contemplated by the present invention, that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more". All structural and functional equivalents to the elements of the above-described preferred embodiment that are known or later come to be known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. §112, sixth paragraph, unless the element is expressly recited using the phrase "means for".

What is claimed is:

1. A shipping package for an electrophoresis gel, comprising:
    at least one gel;
    a housing defining a cover, a holder defining an interior surrounding the gel, and a hinge joining the cover to the holder to permit moving the cover relative to the holder between a closed configuration of the housing, wherein the gel is not exposed and wherein the gel is held in the housing, and an open configuration of the housing, wherein the gel is exposed for removal thereof from the holder; and
    a tray holding the gel, wherein the tray includes one or more side walls, each defining a top edge, the gel being disposed in the tray below the top edges of the side walls, and further wherein the cover is formed with a land closely receivable between the side walls when the housing is in the closed configuration, the land defining a bottom surface, the bottom surface being closely spaced from the gel when the housing is in the closed configuration to thereby limit motion of the gel within the package.

2. The package of claim 1, wherein the tray is closely received in the interior of the holder, the housing being made of a single unitary piece of semi-rigid plastic.

3. The package of claim 2, wherein the tray is made of a rigid UV transparent material.

4. The package of claim 2, wherein the tray defines a contour, and the interior of the holder includes at least one cavity having a contour configured like the contour of the tray, the cavity being marginally larger than the tray to limit motion of the gel relative to the tray.

5. The package of claim 4, wherein the contour of the cavity includes opposed finger depressions for receiving a person's fingers therein to permit the person to grip the tray to remove the tray from the holder.

6. The package of claim 1, wherein the cover defines a surface bounding the land, and at least a portion of the surface contacts the top edges of the side walls of the tray when the housing is in the closed configuration.

7. The package of claim 6, wherein the holder defines a cavity bounded by a surface defining a periphery and the surface of the cover is bounded by one or more raised edges, and the periphery of the surface of the holder engages the raised edges of the cover in an interference fit to hold the housing in the closed configuration.

8. A device for protectively shipping electrophoresis gel, comprising:
    at least one tray holding a gel, the tray including at least one side wall, the wall defining a top edge, the gel being disposed in the tray below the top edge;
    at least one electrophoresis gel disposed in the tray; and
    a non-flaccid clamshell selectively holding the tray with gel, the clamshell including at least one land closely juxtaposable with the at least one side wall, the land defining a bottom surface, the bottom surface being closely spaceable from the gel.

9. The device of claim 8, wherein the clamshell is established by a housing made of semi-rigid plastic, the housing including:
    a cover;
    a holder defining an interior surrounding the gel; and
    a hinge joining the cover to the holder to permit moving the cover relative to the holder between a closed configuration, wherein the gel is not exposed and wherein the gel is held in the housing, and an open configuration, wherein the gel is exposed for removal thereof from the holder.

10. The device of claim 9, wherein the tray is made of a rigid UV transparent acrylic material and the housing is made of polyvinylchloride.

11. The device of claim 9, wherein the tray defines a contour, and the interior of the holder includes at least one cavity having a contour configured like the contour of the tray, the cavity being marginally larger than the tray to limit motion of the gel relative to the tray.

12. The device of claim 11, wherein the contour of the cavity includes opposed finger depressions for receiving a person's fingers therein to permit the person to grip the tray to remove the tray from the holder.

13. The device of claim 11, wherein the tray includes plural side walls, each defining a top edge, the gel being disposed in the tray below the top edges of the side walls, and further wherein the land is closely receivable between the side walls when the device is in the closed configuration, the land defining a bottom surface, the bottom surface being closely spaced from the gel when the device is in the closed configuration to thereby limit motion of the gel.

14. The device of claim 13, wherein the cover defines a surface bounding the land, and at least a portion of the surface contacts the top edges of the side walls of the tray when the device is in the closed configuration.

15. The kit of claim 14, wherein the cavity of the holder is bounded by a surface defining a periphery and the surface of the cover is bounded by one or more raised edges, and the periphery of the surface of the holder engages the raised edges of the cover in an interference fit to hold the housing in the closed configuration.

16. A method for transporting electrophoresis gel, comprising the acts of:

supporting the gel on a tray defining at least one side wall in turn defining a top edge, the gel being disposed in the tray below the top edge;

providing a plastic housing having an open configuration and a closed configuration, the housing including at least one land closely juxtaposable with the at least one side wall, the land defining a bottom surface, the bottom surface preventing motion of the gel away from the tray;

moving the housing to the open configuration;

disposing the gel in the housing; and moving the housing to the closed configuration to completely enclose the gel with the land preventing motion of the gel.

17. The method of claim 16, wherein the moving acts are accomplished by hinged motion.

18. The method of claim 17, wherein the housing is not flaccid.

* * * * *